United States Patent
Lundqvist et al.

(10) Patent No.: US 7,193,718 B2
(45) Date of Patent: Mar. 20, 2007

(54) WAVELENGTH MODULATION SPECTROSCOPY METHOD AND SYSTEM

(75) Inventors: Stefan Lundqvist, Askim (SE); Per-Arne Thorsén, Öjersjö (SE)

(73) Assignee: Siemens Aktiengesellschaft, Munich (DE)

( * ) Notice: Subject to any disclaimer, the term of this patent is extended or adjusted under 35 U.S.C. 154(b) by 350 days.

(21) Appl. No.: 10/839,503

(22) Filed: May 5, 2004

(65) Prior Publication Data

US 2004/0223158 A1 Nov. 11, 2004

(30) Foreign Application Priority Data

May 9, 2003 (EP) ................................. 03010520

(51) Int. Cl.
*G01N 21/00* (2006.01)

(52) U.S. Cl. ...................................... 356/437; 250/343

(58) Field of Classification Search ................ 356/437, 356/409, 326, 324–325, 300, 318; 250/343–344, 250/351; 324/96, 500–501, 752; 378/53
See application file for complete search history.

(56) References Cited

U.S. PATENT DOCUMENTS

| | | | |
|---|---|---|---|
| 4,594,511 A | 6/1986 | Cooper et al. | |
| 5,267,019 A * | 11/1993 | Whittaker et al. | .......... 356/437 |
| 5,969,825 A | 10/1999 | Bomse et al. | |
| 6,040,914 A | 3/2000 | Bortz et al. | |
| 6,351,309 B1 * | 2/2002 | Bomse et al. | ................ 356/437 |
| 6,356,350 B1 | 3/2002 | Silver et al. | |

OTHER PUBLICATIONS

James M. Supplee, Edward A. Whittaker and Wilfred Lenth, "Theoretical Description of Frequency Modulation and Wavelength Modulation Spectroscopy", Applied Optics, Optical Society of America, Washington, DC, US, vol. 33, No. 27, Sep. 20, 1994, pp. 6294-6302, XP000469280.

* cited by examiner

*Primary Examiner*—Layla G. Lauchman
*Assistant Examiner*—Tri Ton

(57) ABSTRACT

In a wavelength modulation spectroscopy method and system the wavelength of a light source is modulated with a frequency $f_0$. The light of the light source is passed to a sample for interacting and thereafter detected and demodulated at a higher harmonic $Nf_0$. To suppress non-linearities in the modulation of the wavelength of the light source a portion of the light (15) of the light source (14) is passed to a monitor detector (17). The monitor detector output is demodulated at said higher harmonic $Nf_0$, and the modulation of the light source (14) is predistorted at said higher harmonic $Nf_0$ in dependence on said demodulated monitor detector output.

10 Claims, 1 Drawing Sheet

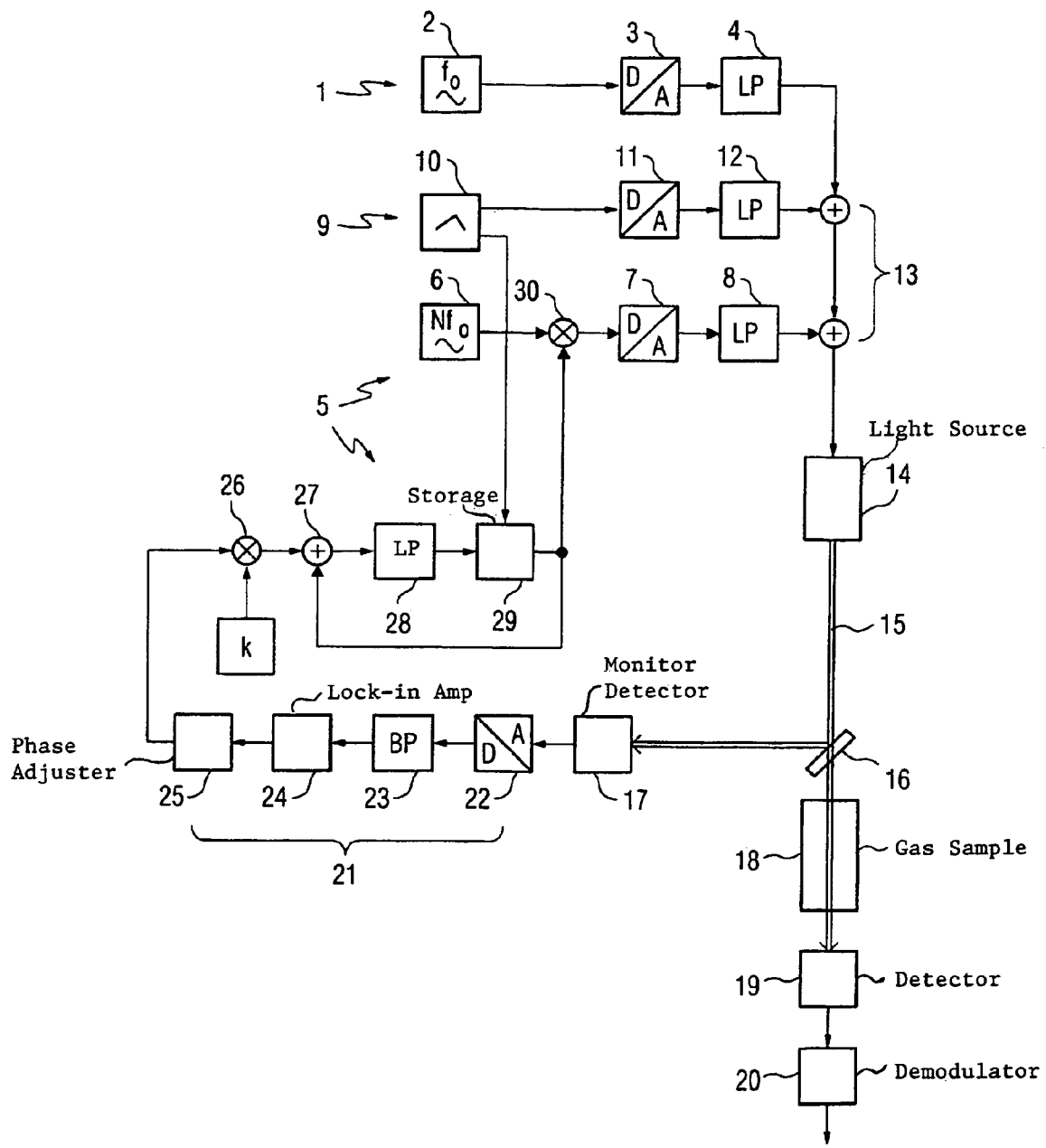

WAVELENGTH MODULATION SPECTROSCOPY METHOD AND SYSTEM

CROSS REFERENCE TO RELATED APPLICATIONS

This application claims priority of European application No. 03010520.9 filed May 9, 2003 and which is incorporated by reference herein in its entirety.

FIELD OF INVENTION

The invention relates to a wavelength modulation spectroscopy method. It further relates to a wavelength modulation spectroscopy system.

BACKGROUND OF INVENTION

In wavelength modulation spectroscopy (WMS) the wavelength of a tunable light source, usually a continuously tunable laser such as a diode laser, is modulated by a small amount about an interaction feature of a sample to be measured, for example a molecular absorption line in a gas sample. The modulation frequency is $f_0$. As the light interacts with the sample, for example propagates through a gas sample, wavelength dependent interaction such as absorption converts some of the wavelength modulation into an amplitude modulation of the light. Thus, the light will have an overtone spectrum generated by the interaction process, the harmonic content of the spectrum being depend on the interaction feature, for example the width and shape of the molecular absorption line in the gas and the etalons in the system. When the light impinges onto a detector, for example a photodiode, the detector output contains AC components at the modulation frequency $f_0$ and its higher harmonics $Nf_0$ (N=2, 3, 4, etc.). Demodulating the detector output at one of said higher harmonics $Nf_0$ shifts the measurement from frequencies near DC, where the light source is noisy, into a higher frequency range, where the noise is lower, thus improving the measurement sensitivity.

From US-A-6040914 a wavelength modulation spectroscopy method and system are known in which a portion of the light of a tunable light source passes through a sample to a measuring detector, whereas another portion of the light directly impinges onto a monitor detector. The measuring detector output and the monitor detector output are fed to an autobalancing circuit, the output of which is demodulated at the double frequency Nf0.

US-B-635 1309 shows a further wavelength modulation spectroscopy method and system, in which a portion of the light is directed through the sample to the measuring detector and in which another portion of the light is directed through reference gas to a reference detector, the reference gas containing the gas species to be measured in the sample. There is however no monitor detector for directly detecting the light of the light source.

Another wavelength modulation spectroscopy method and system which are known from US-B-6356350 do not have a monitor detector either.

To realize a high measurement sensitivity requires the use of expensive highly linear diode laser sources. It would be a great advantage to be able to use inexpensive and widely available communication grade lasers instead, but the non-linearity of the diode laser generates harmonics interfering with the detected harmonics and induces a fluctuation of the baseline, which limits the sensitivity of the measurement.

The noise sources of a diode laser can be divided into deterministic noise and random noise. The most prominent random noise sources are shot noise and flicker (1/f) noise. The deterministic noise has its source of origin in the non-linearity of the laser I-P characteristics (I is the injection current and P is the output power) and the coupling between the laser and fiber and in other optical components. The sensitivity obtained in tunable diode laser spectroscopy is mainly limited by deterministic noise with the random noise being several orders of magnitude lower. The interference phenomena introduced by the deterministic noise are manifested as optical wavelength selective fading causing generation of $Nf_0$ harmonics similar to the ones caused by the wavelength dependent interaction of the sample to be measured.

SUMMARY OF INVENTION

Therefore, the object of the invention is to provide a wavelength modulation spectroscopy method and system, which effectively compensate non-linearities in the modulation of the wavelength of the light source and which are easy to implement.

According to the invention this is achieved by the method defined in claim 1 and the system defined in claim 6.

Preferred embodiments of the method and the system according to the invention are specified in the remaining claims.

In accordance with the invention non-linearities in the modulation of the wavelength of the light source are suppressed by detecting the light before interaction with the sample at the $Nf_0$ harmonic and, in dependence thereon, actively predistorting the modulation input of the light source at said $Nf_0$ harmonic. This will linearize the light source with respect to its output, including the light source as such, for example a diode laser, and any other optical component, for example optical coupling and fiber, between the light source and the monitor detector.

BRIEF DESCRIPTION OF THE DRAWING

The invention will be now described by way of a preferred example and with reference to the only FIGURE of the drawing.

DETAILED DESCRIPTION OF INVENTION

In a first modulation means 1 a digital waveform generator 2 generates a bit stream representing a sinusoidal signal at a frequency $f_0$. The bit stream is converted by a digital-to-analog converter 3 and after that filtered by a low-pass filter 4.

In a second modulation means 5 a second digital waveform generator 6 provides a bit stream representing a sinusoidal signal at a frequency $Nf_0$, which signal is fed via a multiplication means 30 to a digital-to-analog converter 7 and after that to a low-pass filter 8.

In a third modulation means 9 a third digital waveform generator 10 provides a bit stream representing a slow sweep function, which may be part-wise linear in time or of an arbitrary shape. It also generates an address domain defining the range for this slow sweep function. The bit stream is converted to analog form by a digital-to-analog converter 11 and after that filtered by a low-pass filter 12.

The analog signals of said first, second and third modulation means 1, 5, 9 are summed in adding means 13 and fed to a modulation input of a wavelength tunable light source 14 in form of a diode laser.

The light 15 of the light source 14 is split by means of a beam splitter 16 in one portion to a monitor detector 17 and another portion for interacting with a sample 18. According to the slow sweep function of the third digital waveform generator 10 the wavelength of the light 15 sweeps over an interaction feature of the sample 18. Here, a molecular absorption line of interest of a gas sample 18 is scanned. Due to the wavelength dependent absorption the light 15 will have an overtone spectrum, the harmonic content of the spectrum being depend on the width and shape of the molecular absorption line. After passing the gas sample 18 the light 15 impinges onto a detector 19. The detector output, which contains AC components at the modulation frequency $f_0$ and its higher harmonics $2f_0$, $3f_0$, $4f_0$, etc., is demodulated in first demodulation means 20 at the above mentioned higher harmonic $Nf_0$, which shifts the measurement from frequencies near DC, where the light source 14 is noisy, into a higher frequency range, where the noise is lower, thus improving the measurement sensitivity.

The output from the monitor detector 17 is fed to a second demodulation means 21 comprising an analog-to-digital converter 22, a band-pass filter 23, a lock-in amplifier 24 and a phase adjusting means 25 for successively digitizing the monitor detector output, then band-pass filtering the digitized monitor detector output with an $Nf_0$ center frequency in order to eliminate any residual amplitude modulation at $f_0$, converting it to base band and then phase adjusting the lock-in amplifier output.

The phase adjusted lock-in amplifier output is fed to a multiplication means 26 for multiplying with a constant k and then via adding means 27 and a FIR (finite impulse response) low-pass filter 28 to a storage means 29. The storage means 29 comprises a look-up table containing a given number M of values $L_m$ (m=1, . . . , M), which are allocated to and selectable by the same number of different values or positions of the sweep function of the third waveform generator 10.

In the multiplication means 30 the sinusoidal $Nf_0$ signal provided by the second digital waveform generator 6 is multiplied with the output of the storage means 29, i. e. with the stored value assigned to the current position of the sweep function. Thus, the modulation of the light source 14 is predistorted at each position of the sweep with the frequency $Nf_0$ and with an individual amount. By feeding back the output of the storage means 29 to the adding means 27 a fraction k of the demodulated monitor detector output $x_{m,u}$ at the current position m of the sweep function for the current sweep period u is added to the previous value $L_{m,u-1}$, in the storage means 29 and thus an integrator is established with k being the integration constant.

$$L_{m,u}=L_{m,u-1}+k \cdot x_{m,u} \quad \text{(Equation 1)}$$

In the following let $P_{OUT_{Nxf_0}}(v_m)$ represent the laser output power, $P_{D_{Nxf_0}}(v_m)$ the distortion power to be compensated, and $P_{M_{Nxf_0}}(v_m)$ the modulation power applied for compensation, around $Nf_0$ for optical frequency $v_m$ (the optical frequency $v_m$ depends on the current position m of the sweep function).

From $$P_{OUT_{Nxf_0}}(v_m)=P_{D_{Nxf_0}}(v_m)+P_{M_{Nxf_0}}(v_m) \quad \text{(Equation 2)}$$

and $$P_{M_{Nxf_0}}(v_m) = -\frac{1}{s} C_A \cdot k \cdot P_{OUT_{Nxf_0}}(v_m) \quad \text{(Equation 3)}$$

one obtains $$P_{OUT_{Nxf_0}}(v_m) = \frac{\frac{s}{C_A \cdot k} \cdot P_{D_{Nxf_0}}(v_m)}{1 + \frac{s}{C_A \cdot k}}. \quad \text{(Equation 4)}$$

In the expressions above, s is the Laplace operator, 1/s represents integration in the storage means 29 (formally this should be a time discrete expression, but since the input has a very low bandwidth due to the quasi-stationary characteristics of the optical phenomena, the time continuous approximation is valid) and $C_A$ is an instrumentation constant representing analogue gain and scaling within the signal processing chain.

Equation 4 is an expression for a first order high-pass filter where the bandwidth equals the product $C_A \cdot k$. This means that $Nf_0$ distortion components for any optical frequency varying at a lower rate than this bandwidth will be attenuated according to this filter's response.

The FIR low-pass filter 28 provides spatial stability by preventing adjacent values in the storage means 29 to grow too far apart.

The main advantages realized by this invention are:

Unwanted signal components are removed before the light enters the gas to be analyzed. The compensation of the baseline variations is therefore not depend on the transmission in the measurement channel.

The removal of distortions at $Nf_0$ prevents rapid transmission fluctuations to be interpreted as molecular absorption.

The invention is easy to implement in existing technology using well-known standard digital signal processing methods. For example, all digital processing can be performed in an ASIC (application specific integrated circuit), DSP (digital signal processor) or FPGA (field programmable gate array).

The new method of the invention is easy to combine with other methods for reduction of unwanted signals, e. g. with the so-called dual beam subtraction method in order to reduce out of band unwanted signals (residual AM).

The low bandwidth of the new method makes it suitable for implementation in the digital domain, allowing intelligent control of the linearization mechanism. Parameter changes for adoption to different components and operating conditions may therefore easily be implemented and put under software control. Artifact non-linearities and lineshapes may also straightforwardly be inserted for production testing and/or component characterization purposes.

The invention claimed is:

1. A wavelength modulation spectroscopy method, comprising: modulating the wavelength of a light source with a frequency; passing a portion of the light of the light source to a sample for interacting and thereafter to a measuring detector; demodulating the measuring detector output at a higher harmonic of the frequency; passing another portion of the light of the light source to a monitor detector; demodulating the monitor detector output at the higher harmonic of the frequency; and further modulating the light source with the higher harmonic, wherein the modulation intensity is dependent on the demodulated monitor detector output, and the dependence comprises an integration of the demodulated monitor detector output, and further wherein the step of further modulating the light source with the higher harmonic in dependence on said monitor detector output comprises: adding the demodulated monitor detector output or a fraction thereof to a value stored in a storage mechanism; and multiplying said higher harmonic with said updated value; and storing the updated value in a wavelength modulation spectroscopy system in order to measure a sample.

2. The method according to claim 1, further comprising:
periodically sweeping the wavelength of the light source over an interaction feature of the sample according to a sweep function; and
modulating the light source with the higher harmonic in further dependence on the current value of the sweep function.

3. The method according to claim 1, further comprising:
periodically sweeping the wavelength of the light source over an interaction feature of the sample according to a sweep function; and
modulating the light source with the higher harmonic in further dependence on the current value of the sweep function.

4. The method according to claim 1, further comprising:
periodically sweeping the wavelength of the light source over an interaction feature of the sample according to a sweep function; and
modulating the light source with the higher harmonic in further dependence on the current value of the sweep function.

5. The method according to claim 1, further comprising:
periodically sweeping the wavelength of the light source over an interaction feature of the sample according to a sweep function; and
modulating the light source with the higher harmonic in further dependence on the current value of the sweep function, wherein
the storage mechanism contains a given number of values, which are allocated to the same number of different values of the sweep function, and wherein
each of the values in the storage mechanism is selected for updating in dependence on the current value of the sweep function.

6. A wavelength modulation spectroscopy system, comprising:
a wavelength tunable light source;
a first modulation mechanism for modulating the wavelength of the light source with a frequency;
a measuring detector for detecting a portion of the light of the light source after interaction with a sample and producing a measuring detector output;
a first demodulation mechanism for demodulating the measuring detector output at a higher harmonic of the frequency;
a monitor detector for detecting another portion of the light of the light source and producing a monitor detector output;
a second demodulation mechanism for demodulating the monitor detector output at the higher harmonic of the frequency; and a second modulation mechanism for further modulating said light source with the higher harmonic, wherein the second modulation mechanism comprises an integrator mechanism for integrating said demodulated monitor detector output and the modulation intensity is dependent on the demodulated monitor detector output, wherein the integrator mechanism comprises:
a storage mechanism having a value;
an adding mechanism for updating the stored value by adding the demodulated monitor detector output or a fraction thereof; and
a multiplication mechanism for multiplying the higher harmonic with the updated value.

7. The system according to claim 6, further comprising:
a third modulation mechanism for periodically sweeping the wavelength of the light source over an interaction feature of the sample according to a sweep function, wherein
the second modulation mechanism comprises a mechanism for modulating the wavelength of the light source with the higher harmonic in further dependence on the current position of the sweep function.

8. The system according to claim 7, wherein the integrator mechanism comprises:
a storage mechanism having a value;
an adding mechanism for updating the stored value by adding the demodulated monitor detector output or a fraction thereof; and
a multiplication mechanism for multiplying the higher harmonic with the updated value, wherein
the storage mechanism comprises a given number of values, which are allocated to the same number of different positions of the sweep function, and wherein
the second modulation mechanism further comprises a selecting mechanism for selecting each of the values in the storage mechanism in dependence on the current position of the sweep function, the selected value to be updated.

9. The system according to claim 6, further comprising:
a third modulation mechanism for periodically sweeping the wavelength of the light source over an interaction feature of the sample according to a sweep function, wherein
the second modulation mechanism comprises a mechanism for modulating the wavelength of the light source with the higher harmonic in further dependence on the current position of the sweep function.

10. The system according to claim 6, further comprising:
a third modulation mechanism for periodically sweeping the wavelength of the light source over an interaction feature of the sample according to a sweep function, wherein
the second modulation mechanism comprises a mechanism for modulating the wavelength of the light source with the higher harmonic in further dependence on the current position of the sweep function.

* * * * *